United States Patent [19]

Sauer

[11] Patent Number: 5,624,428
[45] Date of Patent: Apr. 29, 1997

[54] ABSORBENT ARTICLE HAVING A PANTLIKE PULL DOWN FEATURE

[75] Inventor: Barbara O. Sauer, Fremont, Wis.

[73] Assignee: Kimberly-Clark Corporation, Neenah, Wis.

[21] Appl. No.: 564,770

[22] Filed: Nov. 29, 1995

[51] Int. Cl.⁶ .................................................. A61F 13/15
[52] U.S. Cl. ........................ 604/391; 604/393; 604/396
[58] Field of Search .................................. 604/385.1–398

[56] References Cited

U.S. PATENT DOCUMENTS

| | | | |
|---|---|---|---|
| 4,074,716 | 2/1978 | Schaar | 604/385.2 |
| 4,596,055 | 6/1986 | Aach et al. | 2/237 |
| 4,663,220 | 5/1987 | Wisneski et al. | 428/221 |
| 4,798,603 | 1/1989 | Meyer et al. | 604/378 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,226,992 | 7/1993 | Mormon | 156/62.4 |
| 5,368,584 | 11/1994 | Clear et al. | 604/393 |
| 5,370,634 | 12/1994 | Ando et al. | 604/385.1 |

FOREIGN PATENT DOCUMENTS

| | | |
|---|---|---|
| 0217032 | 4/1987 | European Pat. Off. . |
| 0544703 | 9/1994 | European Pat. Off. . |
| 6-77718 | 11/1994 | Japan . |

OTHER PUBLICATIONS

U.S. Application No. 08/096,654 filed Jul. 22, 1993, in the name of Hanson et al. entitled "Thin Absorbent Article Having Rapid Uptake of Liquid."

*Primary Examiner*—Robert A. Clarke
*Attorney, Agent, or Firm*—Jeffrey B. Curtin

[57] ABSTRACT

Disclosed is a distinctive absorbent article which includes a pair of fastening means which are located along the longitudinal side portions of the absorbent article. The fastening means are configured to releasably connect the rear portion of the absorbent article to the front portion of the absorbent article to encircle the waist of the wearer and create a waist opening. At least one of the fastening means includes a primary fastener and a secondary fastener. The primary fastener is configured to releasably connect the rear portion of the absorbent article with the front portion of the absorbent article to maintain the absorbent article in a close conforming fit about a waist of a wearer when in use. The secondary fastener is configured to allow the waist opening of the article to expand while still maintaining the rear portion of the absorbent article releasably connected to the front portion of the absorbent article after the primary fastener has been disengaged such that the absorbent article can be pulled up or down over the wearer's hips.

21 Claims, 4 Drawing Sheets

ABSORBENT ARTICLE HAVING A PANTLIKE PULL DOWN FEATURE

BACKGROUND OF THE INVENTION

1. Field of the Invention

The present invention relates to an absorbent article which includes a pantlike pull down feature. The invention more particularly relates to an absorbent article which includes a pair of fastening means which allow the waist opening of the article to expand a sufficient amount such that the absorbent article not only provides a close conforming fit but also can be pulled up or down over the hips of the wearer.

2. Description of the Related Art

It is desired that absorbent articles such as diapers, training pants or incontinence garments provide a close, comfortable fit about the wearer and contain body exudates. Moreover, it is also desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer to easily remove the article if it has not been soiled. For example, such absorbent articles can assist in the toilet training of children.

Conventional diapers have typically included a front waist portion and a rear waist portion which are releasably connected about the hips of the wearer using conventional fasteners such as adhesive tape fasteners and hook and loop type fasteners. Such conventional diapers are easy to fasten about and remove from the wearer after use without undesirably soiling the care giver. The fasteners on such conventional diapers are adapted to secure the diaper about the wearer such that the diaper conforms to the body of the wearer to effectively contain body exudates. However, such conventional diapers typically are not capable of being pulled up or down over the hips of the wearer when the fasteners are attached. Several attempts have been made to provide absorbent articles which effectively contain body exudates and are capable of being pulled up or down over the hips of the wearer. For example, some conventional absorbent articles, such as conventional training pants, have included side panels which connect the front waist portion to the rear waist portion of the absorbent article. The side panels have been made stretchable such that the waist opening of the absorbent article can expand to allow the absorbent article to be pulled up or down over the hips of the wearer if desired. Such side panels have also been designed such that they may be torn to assist in removing the absorbent article from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. As a result, many of such articles have not contained bodily exudates as effectively as conventional diaper-type articles which can be adjusted to achieve a more conforming fit to the wearer.

Accordingly, despite the attempts to develop improved absorbent articles, there remains a need for absorbent articles which effectively contain bodily exudates, which are capable of being pulled up and down over the hips and buttocks of the wearer, and which are readily secured about and removed from the wearer in a convenient and clean manner.

SUMMARY OF THE INVENTION

In response to the difficulties and problems discussed above, a new absorbent article which includes a pantlike pulldown feature has been discovered.

In one aspect, the present invention provides an absorbent article which includes a front portion, a rear portion, a crotch portion which extends between and connects the front portion to the rear portion and a pair of longitudinal side portions. The absorbent article includes a pair of fastening means which are located along said longitudinal side portions of the absorbent article. The fastening means are configured to releasably connect the rear portion of the absorbent article to the front portion of the absorbent article to create a waist opening. At least one of the fastening means comprises a primary fastener and a secondary fastener. The primary fastener is configured to releasably connect the rear portion to the front portion of the absorbent article to maintain the absorbent article about a waist of a wearer when in use. The secondary fastener is configured to maintain the rear portion releasably connected to the front portion after the primary fastener has been disengaged in such a manner that allows the waist opening of the absorbent article to expand such that the absorbent article can be pulled up or down over the wearers hips.

In another aspect, the present invention provides a distinctive absorbent article which includes a front portion, a rear portion, a crotch portion which extends between and connects the front portion to the rear portion, and a pair of longitudinal side portions. The absorbent article includes a pair of fastening means which are located along the longitudinal side portions of the absorbent article. The fastening means am configured to releasably connect the rear portion of the absorbent article to the front portion of the absorbent article to create a waist opening in the absorbent article and secure the absorbent article about a waist of a wearer when in use. Each of the fastening means includes a primary fastener, a secondary fastener and an expansion member. The primary fastener is connected to the rear portion of the absorbent article and is releasably engageable with the front portion of the absorbent article to secure the absorbent article about the waist of the wearer when in use. The expansion member includes an attached end which is connected to the rear portion of the absorbent article and a free end which remains unconnected to the rear portion of the absorbent article. The secondary fastener is connected to the free end of the expansion member and is releasably engageable with the front portion of the absorbent article. In use, the secondary fastener is capable of remaining releasably engaged with the front portion of the absorbent article after the primary fastener has been disengaged from the front portion of the absorbent article to allow the waist opening of the absorbent article to expand such that the absorbent article can be pulled up or down over the wearers hips.

In a particular aspect, the waist opening of the absorbent article defines a first waist perimeter dimension when both the primary and the secondary fasteners are releasably engaged and a second waist perimeter dimension when the primary fasteners are disengaged and the secondary fasteners remain releasably engaged which is greater than the first waist perimeter dimension. The second waist perimeter dimension may be at least about 110 percent of the first waist perimeter dimension.

The present invention can advantageously provide an absorbent article which includes a multifunctional fastening means. The fastening means can be used to releasably engage the front and rear portions of the absorbent article to maintain the absorbent article about the waist of the wearer in a similar manner to conventional diapers. The fastening means can also be configured to allow the waist opening of the absorbent article to expand such that the absorbent article can be pulled up or down over the hips of the wearer such as conventional training pants. As a result, the absorbent article of the present invention is designed to conform to the body of the wearer to effectively contain bodily exudates while still being capable of being pulled up or down over the hips of the wearer with relative ease to assist in the toilet training of the wearer. Moreover, the absorbent article of the present invention can advantageously be applied to and removed from the wearer with relative ease and cleanliness.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
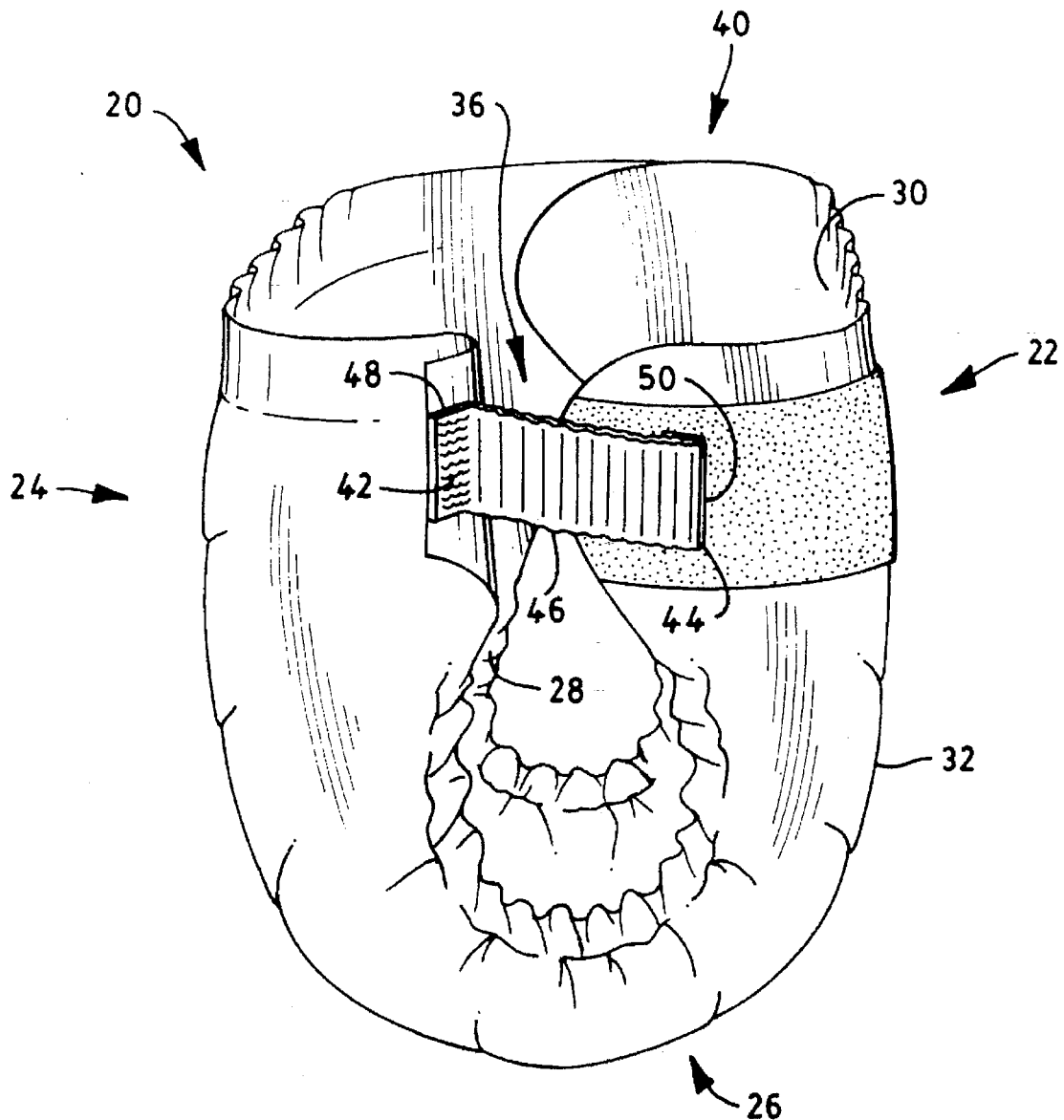
FIG. 1 representatively shows a side elevational view of an example of an absorbent article of the present invention.

The present invention provides an absorbent article which is configured to closely conform to the body of the wearer to effectively contain body exudates while being capable of being pulled up or down over the hips of the wearer. The present invention also provides an absorbent article which can be secured about and removed from the waist of the wearer with relative ease. The absorbent article of the present invention will be described in terms of a diaper or training pant article adapted to be worn by infants about the lower torso. However, it is understood that the absorbent article of the present invention is equally applicable to other articles such as adult incontinent products, feminine care products and the like.

FIGS. 1–5 representatively illustrate an absorbent article 20 of the present invention. The absorbent article 20 defines a front portion 22, a rear portion 24, a crotch portion 26 connecting the front portion 22 and the rear portion 24, and a pair of opposite longitudinal side portions 28. The opposite longitudinal side portions 28 of the absorbent article 20 generally define leg openings which are adapted to fit about the legs of a wearer in use. The absorbent article 20 may include a pair of leg elastics along the longitudinal side portions 28 to provide a snug fit around the leg openings to reduce the likelihood of any leakage therefrom. As used herein, reference to a front portion refers to that part of the absorbent article which is generally located on the front of a wearer when in use, reference to the rear portion refers to the portion of the article generally located at the rear of the wearer when in use, and reference to the crotch portion refers to that portion which is generally located between the legs of the wearer when in use.

The absorbent article 20 includes a bodyside liner 30, an outer cover 32 and an absorbent core 34 located between the bodyside liner 30 and the outer cover 32. The absorbent article 20 further includes a pair of fastening means 36 and 38 which are intended to hold the absorbent article 20 about the waist of the wearer when in use. The fastening means 36 and 38 are located along the longitudinal side portions 28 of the absorbent article 20 and are configured to releasably connect the rear portion 24 of the absorbent article 20 to the front portion 22 of the absorbent article 20 when in use thereby encircling the waist of the wearer and creating a waist opening 40. The absorbent article 20 may further include a waist elastics adjacent the waist opening 40 to further reduce the likelihood of any leakage from the absorbent article 20.

Specific examples of disposable diapers on which the different aspects of the present invention may be utilized are also disclosed in the following U.S. Patents and U.S. Patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al.

Figure 2:
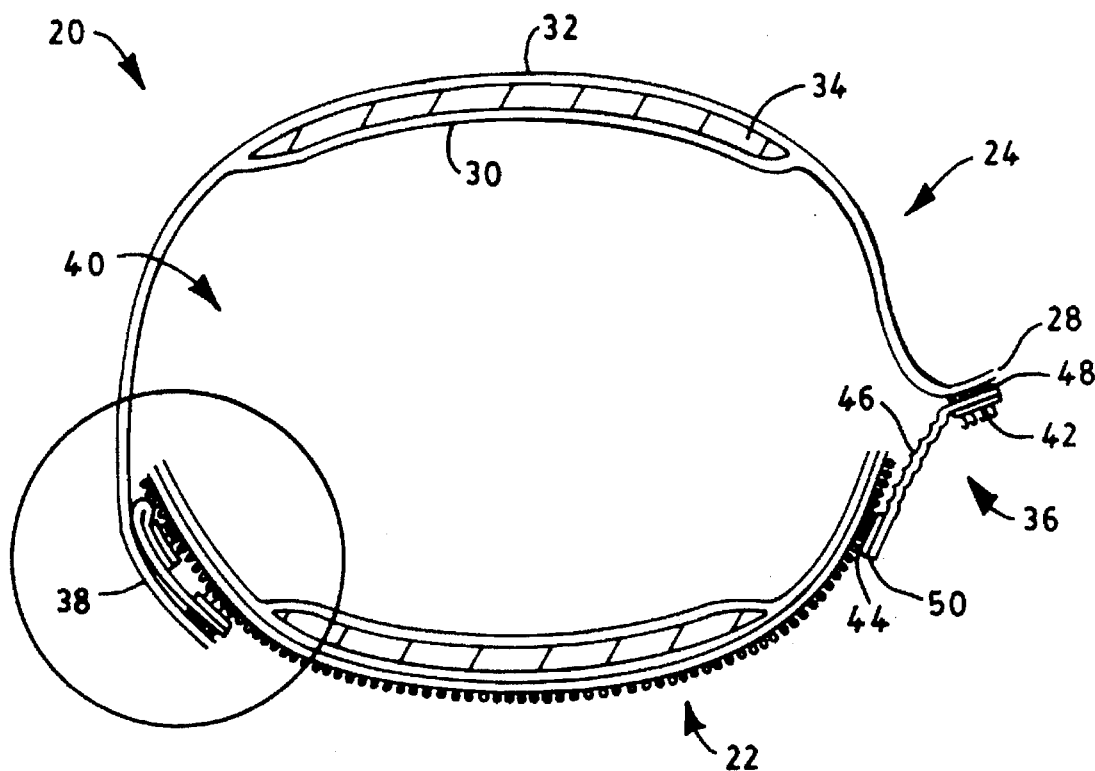
FIG. 2 representatively shows a lateral cross-sectional view of the absorbent article of FIG. 1.
Figure 3:
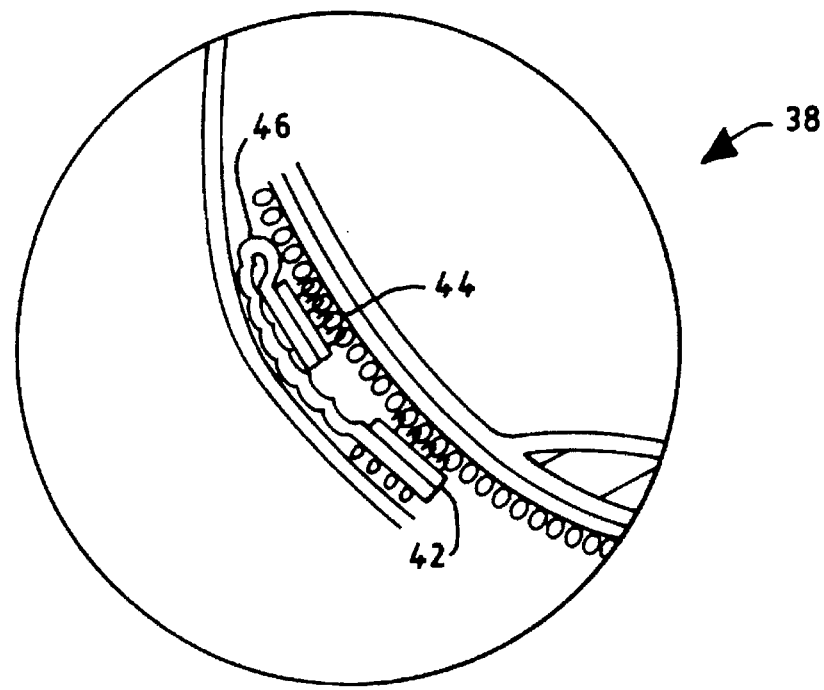
FIG. 3 representatively shows an expanded view of a portion of the absorbent article of FIG. 2.
Figure 4:
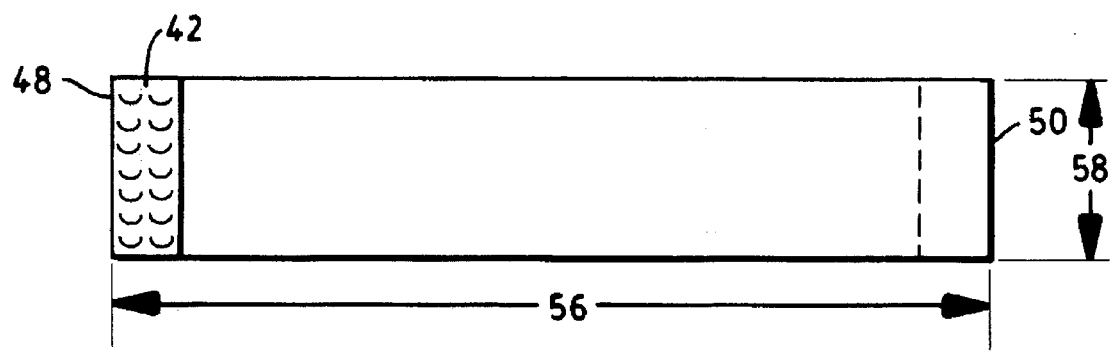
FIG. 4 representatively shows a side elevational view of the fastening means of the absorbent article of FIGS. 1–3.
Figure 5:
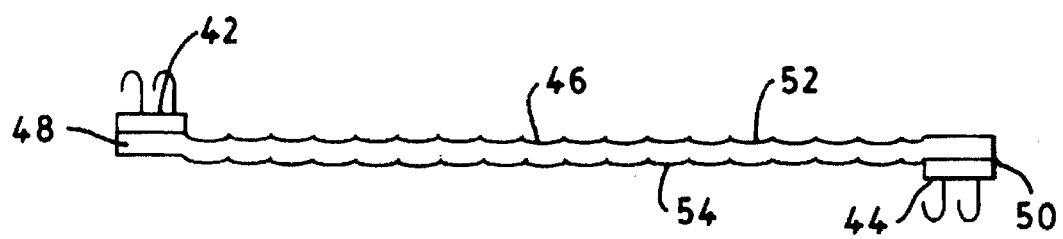
FIG. 5 representatively shows a bottom view of the fastening means of FIG. 4.

The bodyside liner 30 of the absorbent article 20, as representatively illustrated in FIGS. 1–3, suitably presents a bodyfacing surface which is intended to be worn adjacent the body of the wearer and is compliant, soft feeling and nonirritating to the wearer's skin. Further, the bodyside liner 30 may be less hydrophilic than the absorbent core 34, to present a relatively dry surface to the wearer, and may be sufficiently porous to be liquid permeable, permitting liquid to readily penetrate through its thickness. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearers skin from fluids held in the absorbent core 34.

Various woven and nonwoven fabrics can be used for the bodyside liner 30. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 30 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co, under the trade designation Triton X-102.

The outer cover 32 of the absorbent article 20, as representatively illustrated in FIGS. 1–3, may suitably be composed of a material which is either liquid permeable or liquid impermeable. It is generally preferred that the outer cover 32 be formed from a material which is substantially impermeable to fluids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover 32 with a more clothlike feeling, the outer cover 32 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent core 34. Still further, the outer cover 32 may optionally be composed of a micro-porous "breathable" material which permits vapors to escape from the absorbent core 34 while still preventing liquid exudates from passing through the outer cover 32.

The bodyside liner 30 and outer cover 32 are generally adhered to one another so as to form a pocket in which the absorbent core 34 is located. The bodyside liner 30 and outer cover 32 may be adhered directly to each other around the outer periphery of the absorbent article 20 by any means known to those skilled in the art such as adhesive bonds, sonic bonds or thermal bonds, For example, a uniform continuous layer of adhesive, a patterned layer of adhesive, a sprayed or meltblown pattern of adhesive or an array of lines, swirls or spots of adhesive may be used to affix the bodyside liner 30 to the outer cover 32. Such bonding means may also be suitable for attaching other components of the absorbent article of the present invention together. It should be noted that both the bodyside liner 30 and the outer cover 32 need not extend completely to the outer periphery of the absorbent article. For example, the outer cover 32 may extend to the outer periphery of the absorbent article while the bodyside liner 30 may be attached to the outer cover 32 inboard of the outer periphery, or more towards the longitudinal centerline 46, of the absorbent article.

The absorbent core 34, as representatively illustrated in FIGS. 1–3, is positioned between the bodyside liner 30 and the outer cover 32 to form the absorbent article 20. The absorbent core 34 is generally conformable and capable of absorbing and retaining body exudates. The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the absorbent article. It is generally preferred that the absorbent core 34 be narrower in the crotch section of the absorbent core 34 than in the front or back section The absorbent core 34 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 34 may also comprise selected blends of the various types of fibers mentioned above.

In a particular aspect of the invention, the absorbent core 34 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 34 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 34 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 34 of the present invention in an amount of from about 5 to about 95 weight percent and desirably from about 10 to about 60 weight percent based on the total weight of the absorbent core 34. The distribution of the high-absorbency material within the different portions of the absorbent core 34 can vary depending upon the intended end use of the absorbent core 34.

The fastening means 36 and 38 are typically applied to the corners of the rear portion 24 of the absorbent article 20 to provide a means for securing the article 20 about the waist of the wearer. As representatively illustrated in FIGS. 1–5, each of the fastening means 36 and 38 of the present invention includes a primary fastener 42 which is configured to releasably connect the rear portion 24 of the absorbent article 20 to the front portion 22 of the absorbent article 20 to maintain the absorbent article 20 about the waist of the wearer when in use. For example, the primary fastener 42 may be connected to the corners of the rear portion 24 of the absorbent article 20. Such a primary fastener 42 is then releasably engageable with the front portion 22 of the absorbent article 20 to maintain the absorbent article 20 about the wearer. In such a configuration, the primary fastener may be releasably engageable with the bodyside liner 30 or the outer cover 32 of the front portion 22 of the absorbent article 20. Alternatively, the absorbent article 20 may include a separate piece of material or fastener on the front portion 22 of the absorbent article 20 to which the primary fastener 42 can releasably engage. For example, if the primary fastener 42 is a hook type fastener of a hook and loop fastening system, the absorbent article 20 may include a patch of loop material on the front portion 22 of the absorbent article 20.

Suitable fasteners are well known to those skilled in the art and can include tape tab fasteners, hook and loop fasteners, mushroom and loop fasteners, snaps, pins, belts and the like, and combinations thereof. Desirably, the primary fastener 42 is a hook type fastener which is directly releasably engageable with the outer cover 32 of the absorbent article 20 for ease of fastening and improved performance. The primary fastener 42 may be attached to the absorbent article 20 by any means known to those skilled in the art. For example, the primary fastener 42 may be connected to the rear portion 24 of the absorbent article 20 using adhesive bonds, ultrasonic bonds, stitch bonds and the like or combinations thereof. The other components of the fastening means 36 and 38 may also be attached to the absorbent article 20 and/or themselves using similar techniques. The primary fastener 42 is intended to maintain the absorbent article 20 in a close, conforming fit to the wearer to improve the effectiveness of the absorbent article 20 in containing body exudates without leaking.

At least one of the fastening means 36 and 38 of the absorbent article 20 of the present invention also includes a secondary fastener 44 which is configured to selectively maintain the rear portion 24 of the absorbent article 20 releasably connected to the front portion of the absorbent article 20 after the primary fastener 42 has been disengaged. Desirably, both fastening means 36 and 38 include such secondary fasteners 44 as are representatively illustrated in FIGS. 1–5. The secondary fastener 44 of each fastening means 36 and 38 is configured to allow the waist opening 40 of the absorbent article 20 to expand such that the absorbent article 20 may be pulled up or down over the hips of the wearer. The secondary fastener 44 may also be disengaged if desired similar to conventional diaper articles such that the absorbent article 20 can be secured about or removed from the wearer without pulling the absorbent article up or down over the hips of the wearer. The secondary fastener 44 may be any suitable fastener such as those described above as being suitable for the primary fastener 42. The secondary fastener 44 may or may not be the same type of fastener as the primary fastener 42. However, for ease of manufacture and improved performance, it is desirable that the primary and secondary fasteners 42 and 44 are hook type fasteners.

As representatively illustrated in FIGS. 1–5, the secondary fastener 44 may be suitably connected to the corners of the rear portion 24 of the absorbent article 20. For example, each fastening means 36 and 38 may include an expansion member 46 to which the secondary fastener 44 is connected. As representatively illustrated in FIGS. 1–5, the expansion member 46 includes an attached end 48 which is connected to the absorbent article 20 and a free end 50 to which the secondary fastener 44 is attached. The expansion member 46 also defines a first surface 52 and a second surface 54 which is opposite said first surface 52. The combination of the secondary fastener 44 and expansion member 46 is configured to allow the waist opening 40 of the absorbent article 20 to expand when the primary fastener 42 has been disengaged. Such expansion of the waist opening 40 may facilitate the examination of the absorbent article 20 for soiling and the pulling of the absorbent article 40 up or down over the hips of the wearer.

Suitable materials for the expansion member 46 are known to those skilled in the art and may include materials similar to those described for the bodyside liner 30 or outer cover 32 of the absorbent article 20. In a particular embodiment, it is desirable that the expansion member be made of a stretchable or elastic material such that the expansion member 46 can expand while the absorbent article 20 is being pulled up or down over the hips of the wearer. Desirably, the expansion member 46 is made of a stretchable material such that the secondary fastener 44 exerts some tension to hold the article 20 about the waist of the wearer after the primary fastener 42 has been disengaged while at the same time being able to easily stretch to provide the desired expansion of the waist opening 40 for removal.

Suitable stretchable materials are also known to those skilled in the art. For example, the expansion member 46 may be an elasticized material such as a stretch-thermal laminate (STL), neck-bonded laminate (NBL), or stretch-bonded laminate (SBL) material which mat include layers of nonwoven materials. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. Desirably, such stretchable material is capable of being elongated at least about 50 percent and more desirably at least about 200 percent. In a particular example, the expansion member 46 may include a laminate material which includes a meltblown film layer positioned between two spunbond layers and which has a basis weight of about 73 grams per square meter. The meltblown film layer may be composed of meltblown polypropylene fibers and the spunbond layers may be composed of polypropylene fibers. The expansion member 46 may also include bicomponent fibers such as polyethylene/polypropylene bicomponent fibers.

The expansion member 46 of the different aspects of the present invention may have any size and shape which provides the desired expansion of the absorbent article 20. Exemplary of such shapes are rectangular, triangular, square, elliptical and the like. For example, as representatively illustrated in FIGS. 4–5, the expansion member 46 may be rectangular in shape and define a length 56 of at least about 1 centimeter and desirably at least about 2.5 centimeters and a width 58 of from about 1.2 to about 10 centimeters.

The fastening means 36 and 38 of the different aspects of the present invention are configured to allow the waist opening 40 of the absorbent article 20 to expand from its initially applied dimensions such that the absorbent article can be pulled up or down over the hips of the wearer without requiring that the front portion 22 of the absorbent article 20 be disconnected from the rear portion 24 of the absorbent article 20. For example, the expansion may occur when at least one of the primary fasteners 42 is disengaged from the front portion 22 of the absorbent article 20 while the secondary fasteners 44 remain releasably engaged with the front portion 22 of the absorbent article 20 as illustrated in FIG. 1. The amount of expansion of the waist opening 40 can be controlled by the size and shape of the different components of the fastening means 36 and 38, such as the length 56 of the expansion member 46. In a particular embodiment, the fastening means 36 and 38 allows an area of the waist opening 40 of the absorbent article to expand at least about 20 percent, desirably at least about 40 percent and more desirably at least about 80 percent.

As representatively illustrated in FIGS. 1–5, the waist opening 40 defines a first waist perimeter dimension when both primary fasteners 42 are engaged and a second waist perimeter dimension when both primary fasteners are disengaged while the secondary fasteners 44 remain releasably engaged. The second waist perimeter dimension is greater than the first waist perimeter dimension. To assist in pulling the absorbent article 20 up or down over the hips of the wearer, the second waist perimeter dimension is at least about 10 percent and desirably at least about 20 percent of the first waist perimeter dimension. In a particular example wherein the absorbent article 20 includes an expansion member 46 which is stretchable, the second waist perimeter dimension is at least about 20 percent of the first waist perimeter dimension when the expansion member 46 is relaxed and is at least about 40 percent of the first waist perimeter dimension when the expansion member 46 is stretched.

The different components of the fastening means 36 and 38 of the present invention can be configured in any manner which provides the desired expansion of the waist opening 40. For example, as representatively illustrated in FIGS. 1–5, the expansion member 46 may define a first surface 52 and a second surface 54 which is opposite the first surface 52. The second surface 54 of the attached end 48 of the expansion member 46 may be connected to the rear portion 24 of the absorbent article 20. The primary fastener 42 may be connected to the first surface 52 of the expansion member 46 near the attached end 48 of the expansion member 46 for ease of manufacture. Alternatively, the primary fastener 42 may be connected directly to the absorbent article 20. The secondary fastener 44 is connected to the second surface 54 of the free end 50 of the expansion member 46. In such a configuration as is illustrated in FIGS. 1–5, the secondary fastener 44 is subjected to shear type forces when the primary fastener 42 has been disengaged and the absorbent article 20 is being pulled up or down over the hips of the wearer.

Figure 6:
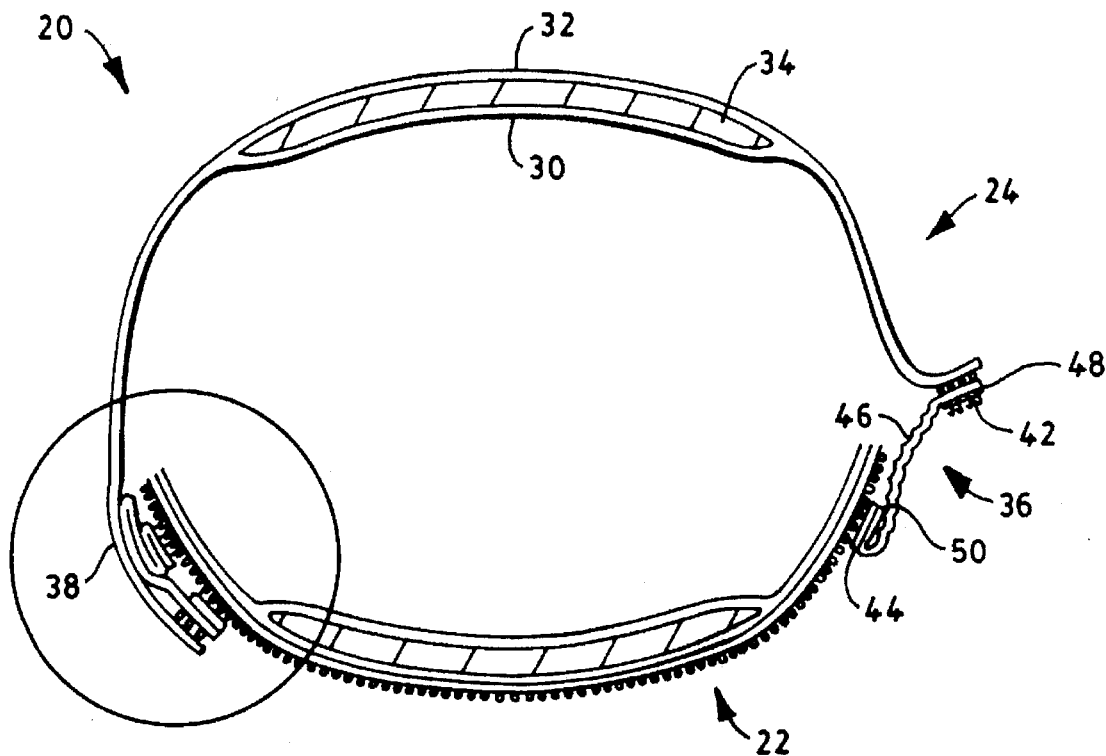
FIG. 6 representatively shows a lateral cross-sectional view of another example of an absorbent article of the present invention.

Desirably, the primary fastener 42 and the secondary fastener 44 of each fastening means 36 and 38 are configured to be positioned adjacent each other when the absorbent article 20 is secured about the waist of the wearer as is representatively illustrated in FIGS. 2 and 6. In such a configuration, the care giver can engage or disengage both the primary and secondary fasteners 42 and 44 with the same motion of one hand if desired for easy fastening and removal. Moreover, when the secondary fastener 44 remains engaged, the secondary fastener 44 can aid in repositioning the primary fastener 42 such that the absorbent article 20 can be accurately repositioned on and secured about the wearer in it's original location if desired. Such use of the secondary fastener 44 as a locating device is particularly beneficial when trying to refasten the primary fastener 42 when the wearer is in a standing position.

Figure 7:
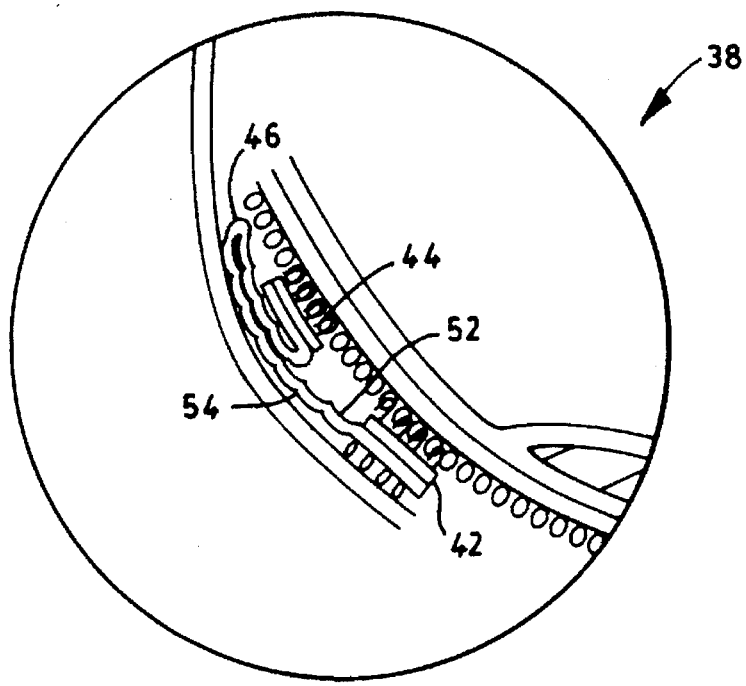
FIG. 7 representatively shows an expanded view of a portion of the absorbent article of FIG. 6.

An alternative configuration of the fastening means 36 and 38 is representatively illustrated in FIGS. 6–7. As illustrated, the primary fastener 42 may be connected to the first surface 52 of the expansion member 46 near the attached end 48 of the expansion member 46 for ease of manufacture. Alternatively, the primary fastener 42 may be connected directly to the absorbent article 20. The second surface 54 of the expansion member 46 may be connected to the rear portion 24 of the absorbent article 20. The secondary fastener 44 is also connected to the first surface 52 of the free end 50 of the expansion member 46. In such a configuration, the secondary fastener 44 is subjected to peel type forces when the primary fastener 42 has been disengaged and the absorbent article 20 is being pulled up or down over the hips of the wearer. Typically, a greater force is required to disengage most hook and loop type fasteners in a shear mode than in a peel mode. Accordingly, if the secondary fasteners 44 are hook and loop type fasteners, it is desirable that the fastening means 36 and 38 have the configuration representatively illustrated in FIGS. 1–5 for more reliable fastening and improved performance.

In such configurations, the primary and secondary fasteners 42 and 44 can be releasably engaged with the front portion 22 of the absorbent article 20 to secure the absorbent article 20 about the waist of the wearer. When in use, the primary fasteners 42 are intended to maintain the absorbent 20 article in a close conforming fit about the waist of the wearer to reduce the leakage of body exudates. The secondary fasteners 44 are intended to maintain the front and rear portions 22 and 24 of the absorbent article connected in such a manner that the article 20 can be secured about or removed from the wearer by pulling the article up or down over the hips of the wearer after the primary fasteners 42 have been disengaged. The primary fasteners 42 may also be selectively disengaged to facilitate inspection of the absorbent article 20 for soiling. The secondary fasteners 44 can also provide a "childproofing function" by maintaining the absorbent article 20 at least partially secured about the waist of the wearer if the wearer undesirably disengages the primary fastener 42.

Thus, the absorbent article of the present invention can be secured about the waist of the wearer by positioning the absorbent article between the legs of the wearer and releasably connecting the fastening means or by releasably connecting the fastening means and then pulling the absorbent article up over the legs and hips of the wearer. Accordingly, the different aspects of the present invention can advantageously provide absorbent articles which are capable of effectively preventing the leakage of body exudates and which are capable of being pulled up or down over the hips and buttocks of the wearer to facilitate toilet training.

Moreover, the absorbent article of the present invention is also easily removed from the waist of the wearer when soiled without undesirably soiling the care giver or the legs of the wearer.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

I claim:

1. An absorbent article which includes a front portion, a rear portion, a crotch portion which extends between and connects said front portion to said rear portion, and a pair of longitudinal side portions, said absorbent article comprising a pair of fastening means which are located along said longitudinal side portions of said absorbent article and which are configured to releasably connect said rear portion of said absorbent article to said front portion of said absorbent article to create a waist opening in said absorbent article and secure said absorbent article about a waist of a wearer when in use wherein each of said fastening means comprises:

a) a primary fastener which is connected to said rear portion of said absorbent article and which is releasably engageable with said front portion of said absorbent article to secure said absorbent article about said waist of said wearer when in use;

b) an expansion member which defines a first surface and a second surface opposite said first surface and which includes an attached end which is connected to said rear portion of said absorbent article and a free end which remains unconnected to said rear portion of said absorbent article; and c) a secondary fastener which is connected to said free end of said expansion member and which is releasably engageable with said front portion of said absorbent article wherein said primary fastener is connected to said first surface of said expansion member at said attached end and said secondary fastener is connected to said second surface of said expansion member at said free end and wherein, in use, said secondary fastener is capable of remaining releasably engaged with said front portion of said absorbent article after said primary fastener has been disengaged from said front portion of said absorbent article to allow said waist opening of said absorbent article to expand such that said absorbent article can be pulled up or down over said wearer's hips.

2. The absorbent article of claim 1 wherein said fastening means are configured to allow an area of said waist opening of said absorbent article to expand at least about 20 percent when said primary fasteners are disengaged from said front portion of said absorbent article and said secondary fasteners remain releasably engaged with said front portion of said absorbent article.

3. The absorbent article of claim 1 wherein said waist opening of said absorbent article defines a first waist perimeter dimension when both said primary and said secondary fasteners are releasably engaged with said front portion of said absorbent article and a second waist perimeter dimension when said primary fasteners are disengaged from said front portion and said secondary fasteners remain releasably engaged with said front portion of said absorbent article and wherein said second waist perimeter dimension is greater than said first waist perimeter dimension.

4. The absorbent article of claim 3 wherein said second waist perimeter dimension is at least about 10 percent of said first waist perimeter dimension.

5. The absorbent article of claim 3 wherein said second waist perimeter dimension is at least about 20 percent of said first waist perimeter dimension.

6. The absorbent article of claim 1 wherein said primary fastener is a hook and loop type fastener.

7. The absorbent article of claim 1 wherein said expansion member is configured to remain in a relaxed condition when said absorbent article is secured about said waist of said wearer.

8. The absorbent article of claim 1 wherein said expansion member is stretchable.

9. The absorbent article of claim 8 wherein said expansion member is configured to elongate at least about 50 percent.

10. The absorbent article of claim 1 wherein said secondary fastener is a hook and loop type fastener.

11. The absorbent article of claim 1 wherein said absorbent article includes:

a) an outer cover;

b) a bodyside liner which is superposed on said outer cover; and c) an absorbent core which is located between said outer cover and said bodyside liner.

12. An absorbent article which includes a front portion, a rear portion, a crotch portion which extends between and connects said front portion to said rear portion, and a pair of longitudinal side portions, said absorbent article comprising a pair of fastening means which are located along said longitudinal side portions of said absorbent article and which are configured to releasably connect said rear portion of said absorbent article to said front portion of said absorbent article to create a waist opening in said absorbent article and secure said absorbent article about a waist of a wearer when in use wherein each of said fastening means comprises:

a) a primary fastener which is connected to said rear portion of said absorbent article and which is releasably engageable with said front portion of said absorbent article to secure said absorbent article about said waist of said wearer when in use;

b) an expansion member which defines a first surface and a second surface opposite said first surface and which includes an attached end which is connected to said rear portion of said absorbent article and a free end which remains unconnected to said rear portion of said absorbent article; and c) a secondary fastener which is connected to said free end of said expansion member and which is releasably engageable with said front portion of said absorbent article wherein said primary fastener and said secondary fastener are connected to said first surface of said expansion member and wherein, in use, said secondary fastener is capable of remaining releasably engaged with said front portion of said absorbent article after said primary fastener has been disengaged from said front portion of said absorbent article to allow said waist opening of said absorbent article to expand such that said absorbent article can be pulled up or down over said wearers hips.

13. The absorbent article of claim 12 wherein said fastening means are configured to allow an area of said waist opening of said absorbent article to expand at least about 20 percent when said primary fasteners are disengaged from said front portion of said absorbent article and said secondary fasteners remain releasably engaged with said front portion of said absorbent article.

14. The absorbent article of claim 12 wherein said waist opening of said absorbent article defines a first waist perimeter dimension when both said primary and said secondary fasteners are releasably engaged with said front portion of said absorbent article and a second waist perimeter dimension when said primary fasteners are disengaged from said front portion and said secondary fasteners remain releasably engaged with said front portion of said absorbent article and wherein said second waist perimeter dimension is greater than said first waist perimeter dimension.

15. The absorbent article of claim 14 wherein said second waist perimeter dimension is at least about 10 percent of said first waist perimeter dimension.

16. The absorbent article of claim 14 wherein said second waist perimeter dimension is at least about 20 percent of said first waist perimeter dimension.

17. The absorbent article of claim 12 wherein said primary fastener is a hook and loop type fastener.

18. The absorbent article of claim 12 wherein said expansion member is configured to remain in a relaxed condition when said absorbent article is secured about said waist of said wearer.

19. The absorbent article of claim 12 wherein said expansion member is stretchable.

20. The absorbent article of claim 19 wherein said expansion member is configured to elongate at least about 50 percent.

21. The absorbent article of claim 12 wherein said secondary fastener is a hook and loop type fastener.

* * * * *